United States Patent
Ludwig et al.

(10) Patent No.: US 9,717,270 B2
(45) Date of Patent: Aug. 1, 2017

(54) FERMENTED INFANT FORMULA WITH NON DIGESTIBLE OLIGOSACCHARIDES

(71) Applicant: N.V. Nutricia, Zoetermeer (NL)

(72) Inventors: Thomas Ludwig, Utrecht (NL); Sylvie Huybers, Utrecht (NL); Evan Abrahamse, Utrecht (NL); Houkje Bouritius, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 15/441,405

(22) Filed: Feb. 24, 2017

(65) Prior Publication Data

US 2017/0156389 A1    Jun. 8, 2017

Related U.S. Application Data

(62) Division of application No. 14/407,907, filed as application No. PCT/NL2013/050419 on Jun. 14, 2013.

(30) Foreign Application Priority Data

Jun. 14, 2012    (WO) ............... PCT/NL2012/050418

(51) Int. Cl.
| | |
|---|---|
| *C07K 14/705* | (2006.01) |
| *A23L 33/00* | (2016.01) |
| *A61K 35/20* | (2006.01) |
| *A61K 31/7004* | (2006.01) |
| *A61K 31/702* | (2006.01) |
| *A61K 31/19* | (2006.01) |
| *A61K 35/744* | (2015.01) |
| *A61K 38/17* | (2006.01) |
| *A61K 31/716* | (2006.01) |
| *A23L 33/135* | (2016.01) |
| *A23L 33/17* | (2016.01) |

(52) U.S. Cl.
CPC ............ *A23L 33/40* (2016.08); *A23L 33/135* (2016.08); *A23L 33/17* (2016.08); *A61K 31/19* (2013.01); *A61K 31/702* (2013.01); *A61K 31/7004* (2013.01); *A61K 31/716* (2013.01); *A61K 35/20* (2013.01); *A61K 35/744* (2013.01); *A61K 38/1709* (2013.01); *A23V 2002/00* (2013.01); *A23Y 2240/75* (2013.01)

(58) Field of Classification Search
None
See application file for complete search history.

(56) References Cited

U.S. PATENT DOCUMENTS

| | | | |
|---|---|---|---|
| 6,358,521 | B1 | 3/2002 | Izvekova et al. |
| 7,410,653 | B1 | 8/2008 | Blareau et al. |
| 8,119,379 | B2 | 2/2012 | Blareau et al. |
| 8,715,769 | B2 | 5/2014 | Schmitt et al. |
| 2004/0072794 | A1 | 4/2004 | Kaup et al. |
| 2005/0180962 | A1 | 8/2005 | Raz et al. |
| 2006/0018890 | A1 | 1/2006 | Isolauri et al. |
| 2006/0233773 | A1 | 10/2006 | Herz et al. |
| 2007/0104700 | A1 | 5/2007 | Garcia-Rodenas et al. |
| 2007/0160589 | A1 | 7/2007 | Mattson |
| 2008/0248056 | A1 | 10/2008 | Petay et al. |
| 2008/0268099 | A1 | 10/2008 | Blareau et al. |
| 2010/0278781 | A1 | 11/2010 | Hougee et al. |
| 2011/0097437 | A1 | 4/2011 | Knol et al. |
| 2011/0182934 | A1 | 7/2011 | Nutricia |
| 2013/0189398 | A1 | 7/2013 | Rosado Loria et al. |

FOREIGN PATENT DOCUMENTS

| | | |
|---|---|---|
| EP | 1 020 123 A1 | 7/2000 |
| EP | 1 145 643 A1 | 10/2001 |
| EP | 1 320 375 B1 | 6/2003 |
| EP | 1 364 586 A1 | 11/2003 |
| EP | 1 535 520 A1 | 6/2005 |
| EP | 1 597 978 A1 | 11/2005 |
| EP | 1 685 763 A1 | 8/2006 |
| EP | 1 776 877 A1 | 4/2007 |
| EP | 1 815 755 B1 | 8/2007 |
| EP | 2 520 181 A1 | 11/2012 |
| WO | WO-01/01785 A1 | 1/2001 |
| WO | WO-01/64225 A1 | 9/2001 |
| WO | WO-02/26242 A2 | 4/2002 |
| WO | WO-2004/052121 A1 | 6/2004 |
| WO | WO-2004/069156 A2 | 8/2004 |
| WO | WO-2004/093898 A2 | 11/2004 |
| WO | WO-2004/093899 A1 | 11/2004 |
| WO | WO-2004/112509 A2 | 12/2004 |
| WO | WO-2005/039319 A1 | 5/2005 |
| WO | WO-2005/039319 A2 | 5/2005 |
| WO | WO-2005/039597 A2 | 5/2005 |
| WO | WO-2006/069918 A1 | 7/2006 |
| WO | WO-2006/087391 A1 | 8/2006 |
| WO | WO-2006/091103 A2 | 8/2006 |
| WO | WO-2007/045502 A1 | 4/2007 |
| WO | WO-2007/046698 A1 | 4/2007 |
| WO | WO-2007/067053 A1 | 6/2007 |
| WO | WO-2008/153377 A1 | 12/2008 |
| WO | WO-2008/153391 A2 | 12/2008 |
| WO | WO-2009/151329 A1 | 12/2009 |
| WO | WO-2009/151330 A1 | 12/2009 |
| WO | WO-2010/008278 A1 | 1/2010 |
| WO | WO-2010/070613 A2 | 6/2010 |
| WO | WO-2012/078030 A1 | 6/2012 |
| WO | WO-2012/078039 A1 | 6/2012 |

OTHER PUBLICATIONS

Alm, "Effects of fermentation on curd size and digestibility of milk proteins in vitro of Swedish fermented milk products", Journal of Dairy Science, Apr. 1982, vol. 65, No. 4, pp. 509-514.

(Continued)

*Primary Examiner* — Robert A Wax
*Assistant Examiner* — Randeep Singh
(74) *Attorney, Agent, or Firm* — Gilberto M. Villacorta; Sunit Talapatra; Foley & Lardner LLP

(57) ABSTRACT

The present invention relates to a fermented infant formulae comprising non digestible oligosaccharides for improving intestinal tract health by decreasing protein digestive effort, by decreasing the amount of endogenously formed proteases concomitant with an increased protein digestion, and a reduced protein fermentation.

11 Claims, No Drawings

(56) References Cited

OTHER PUBLICATIONS

Fanaro et al., "Galacto-oligosaccharides and long-chain fructo-oligosaccharides as prebiotics in infant formulas: A review", Acta Paediatrica, 94 (Suppl 449), 2005, 22-26.

Gronlund, et al. "Maternal breast-milk and intestinal bifidobacteria guide the compositional development of the Bifidobacterium microbiota in infants at risk of allergic disease", Clinical and Experimental Allergy (2007), vol. 37, pp. 1764-172.

Grönlund, Minna-Maija, et al., "Fecal Microflora in Healthy Infants Born by Different Methods of Delivery: Permanent Changes in Intestinal Flora After Cesarean Delivery," Journal of Pediatric Gastroenterology and Nutrition, 28(1):19-25 (1999).

Heyman et al., "Effects of specific lactic acid bacteria on the intestinal permeability to macromolecules and the inflammatory condition," Acta Paediatrica, vol. 94 (Suppl. 449), pp. 34-36 (2005).

Kirjavainen et al., "Probiotic Bacteria in the Management of Atopic Disease: Underscoring the Importance of Viability," Journal of Pediatric Gastoenterology and Nutrition, 36:223-227 (2003).

Life Start® —Dairy (1.25 oz. powder), Natren, The Probiotic Specialist Recognized Worldwide, 2 pgs., (2006).

McVay et al., "Formula Fortified With Live Probiotic Culture Reduces Pulmonary and Gastrointestinal Bacterial Colonization and Translocation in a Newborn Animal Model," Journal of Pediatric Surgery, 43:25-29 (2008).

Menard et al. "Bifidobacterium breve and *Streptococcus* thermophiles secretion products enhance T helper 1 immune response and intestinal barrier in mice", 2005, Exp. Biol. Med. vol. 230, pp. 749-756.

Petay et al., ( WO 2004093899)—Google Machine Translation WIPO, Sep. 28, 2012.

Prosky L, et al., "Determination of Insoluble, Soluble, and Total Dietary Fiber in Foods and Food Products: Interlaboratory Study," J. Assoc. Off. Anal. Chem., 1988, vol. 71, No. 5, pp. 1017-1023.

Reeves P, et al., "Development and Testing of the AIN-93 Purified Diets for Rodents: Results on Growth, Kidney Calcification and Bone Mineralization in Rats and Mice," Journal of Nutrition, 1993, pp. 1923-1993, vol. 123, No. 11.

Sambrook, J., et al.. "Molecular Cloning, A Laboratory Manual," 2nd ed., Cold Spring Harbor (N.Y.) Laboratory Press, 1989.

Savino et al., "Reduction of crying episodes owing to infantile colic: a randomized controlled study on the efficacy of a new infant formula", European Journal of Clinical Nutrition, 2006, vol. 60, pp. 1304-1310.

Scardovi V., "Genus *Bifidobacterium* Orla-Jensen 1924, 472AL," In: Bergey's Manual of Systematic Bacteriology, vol. 2, Williams & Wilkins, Baltimore, 1984, pp. 1418-1434.

Thibault H et al. "Effects of Long-Term Consumption of a Fermented Infant Formula (With Bifidobacterium Breve C50 and *Streptococcus thermophilus* 065) on Acute Diarrhea in Healthy Infants", Journal of Pediatric Gastroenterology and Nutrition, Raven Press, New York, NY vol. 39, No. 2, Aug. 1, 2004.

Vass, A. et al., "Experimental Study of the Nutritional Biological Characters of Fermented Milks," Acta Medica Hungarica, vol. 41, Nos. 2-3, pp. 157-161, 1984.

Vergnolle, "Clinical relevance of proteinase activated receptors (PARS) in the gut", Gut, 2005, vol. 54, pp. 867-874.

FERMENTED INFANT FORMULA WITH NON DIGESTIBLE OLIGOSACCHARIDES

CROSS REFERENCE TO RELATED APPLICATIONS

The present application is a Divisional Application of U.S. patent application Ser. No. 14/407,907, filed Dec. 12, 2014, which is the National Stage of International Application No. PCT/NL2013/050419, filed Jun. 14, 2013, which claims priority to International Application No. PCT/NL2012/050418, filed Jun. 14, 2012. The contents of these applications are herein incorporated by reference in their entirety.

FIELD OF THE INVENTION

The present invention relates to nutritional formulae for infants and toddlers and in particular addresses reduction of proteolytic activity in the intestinal tract, while maintaining or even improving an efficient protein digestion.

BACKGROUND OF THE INVENTION

Digestion of dietary proteins is achieved by the release of proteases from the stomach and the pancreas. The release of proteases is normally tightly regulated, thereby ensuring that not too less and not too much proteolytic enzymes are secreted. This is important since a high release of proteases and a high proteolytic activity has several disadvantages. A too high release of proteases will result in energy loss and a loss of essential amino acids due to the fact that proteases themselves are highly resistant to proteolytic activity and will enter into the colon mostly unaltered. Subsequently, upon entering of an increased amount of protein (in the form of proteases) into the colon, the intestinal microbiota will ferment the proteins resulting in a disadvantageously higher pH, a shift in the composition of the intestinal microbiota and formation of toxic metabolites such as phenol, indol, and amines. This change in colonic physiology may also lead to increased intestinal infections. Finally, proteases such as trypsin are known to cleave protease activated receptors (PARs), such as PAR-II, and thereby disrupt intestinal barrier integrity. This may result in an increased abdominal pain perception. Inflammatory diseases such as IBS-D and UC have been linked to elevated levels of proteolytic activity within the intestinal lumen and subsequent PAR-II activation. Furthermore, increased faecal proteolytic activity is linked to diaper rashes. In general, a too high release of proteases will result in decreasing gastrointestinal comfort, functional digestive disorders, gastrointestinal gas formation, and/or bloating. A too low secretion of proteolytic activity, on the other hand, is disadvantageous since in that case the dietary proteins are not properly digested leading also to loss of essential amino acids and energy, and an increased protein load of the colon.

Especially in infants and toddlers a tight regulation of protein digestion and release of proteolytic activity is of utmost importance. Firstly, for infants and toddlers a limited loss of protein is essential for good growth and development. Loss of essential amino acids and energy impairs growth and development. Secondly, the intestinal barrier function in infants and toddlers is still immature and the intestinal microbiota is still developing and therefore more susceptible for the disadvantages mentioned above. Pain perception e.g. due to colics or cramps often is a great cause of concern and initiates many doctor visits and thus reduction of the risk of pain perception, for example prevention and/or treatment of colics and/or cramps is desired.

Known ways to improve protein digestion, in particular in infants, involve partial predigestion of dietary proteins by proteases. Furthermore, Alm, 1982, J Dairy Sci 65:509-514 discloses that a low pH of milk products, especially as a result of fermentation, has a positive influence on in vitro digestibility of proteins. It is considered that in many digestive disorders the secretion of hydrochloric acid is impaired and thus the suitability of such low pH milk products is suggested for infants, children and adults. Vass et al, 1984, Acta Medica Hungarica, 41, 15-161 disclose that fermented milks have the highest protein utilization index, defined as increase in body mass in g per protein intake in g, in weaning rats, and this is attributed to a better digestibility of proteins.

Gallia Lactofidus® is an acidified infant formula, resulting from fermentation by two specific strains of lactic acid bacteria. It is disclosed that this formula facilitates the digestibility of proteins and improves the intestinal transit.

WO 2009/151330 discloses fermented infant formula with non digestible oligosaccharides for use in improving intestinal colonization in infants born via Caesarean section.

US 2011/097437 discloses nutritional compositions comprising non-digestible oligosaccharides and a protein substrate fermented with *Bifidobacterium breve* and *Streptococcus thermophilus* for use in reduction of bacterial translocation and improvement of intestinal barrier function.

US 2010/278781 discloses a protein comprising composition, fermented by *Bifidobacterium breve* and comprising non-digestible oligosaccharides with several health benefits.

SUMMARY OF THE INVENTION

The inventors have found that, employing piglets as animal model, upon consumption of a fermented formula the amount of endogenous proteolytic enzymes detected at the terminal ileum was significantly reduced compared to the amount detected upon consumption of a standard non fermented formula. Surprisingly, the amount of endogenous proteolytic enzymes was also significantly reduced compared to the amount detected upon consumption of a formula with extensively hydrolysed (i.e. predigested) proteins.

In addition and unexpectedly as well, the apparent and true protein digestibility was the highest in the piglets consuming the fermented formula as well, even though their daily protein intake was higher. This is indicative for a decreased digestive effort. Digestive effort is defined as the amount of protease activity secreted per gram of ingested protein. Digestive efficiency is defined as reciprocal value of digestive effort. This means that at high digestive efficiency (little protease needed to digest the ingested protein) the digestive effort is low.

The inventors further found that the proteolytic activity in faecal samples of exclusively breast fed human infants was lower than that of infants fed with a standard formula. When the formula administered to the human infants comprised non digestible oligosaccharides the proteolytic activity in the faecal samples was lower with similar values as observed for the breast fed human infants.

So, upon feeding a protein comprising fermented formula, the release of endogenous protease, digestive effort, endogenous protein loss in the small intestine and the protein load entering the colon is advantageously reduced. The additional presence of non digestible oligosaccharides reduces the proteolytic activity of the microbiota in the colon. Hence an infant or toddler formula being both fermented and comprising non digestible oligosaccharides will have a further improved effect on reducing protein fermentation and proteolytic activity in the colon. Moreover, an infant or toddler formula being both fermented and comprising non digestible oligosaccharides will have a beneficial effect regarding proteolytic activity reduction along the entire, i.e. both small and large, intestinal tract. Therefore a fermented formula comprising non digestible oligosaccharides is advantageously used as nutrition for infants or toddlers for use in preventing and/or treatment of diaper rashes or in promoting intestinal tract health by reducing digestive effort, improving protein digestion efficiency, reducing endogenous protein loss, reducing endogenous secretion of proteases, reducing colonic protein fermentation and/or reducing the protein load entering the colon.

The finding that protein digestion efficiency is increased, and endogenous protein loss is decreased also advantageously enables the formulation of an infant [or toddler] formula with lower protein concentrations than used so far.

DETAILED DESCRIPTION OF THE INVENTION

The present invention concerns a method, in particular a non-therapeutic method, for
a increasing protein digestion efficiency,
b reducing secretion of proteases in the small and/or large intestine,
c reducing proteolytic activity in the small and/or large intestine,
d reducing the protein load entering the large intestine and/or
e reducing the fermentation of protein in the large intestine
in a human subject with an age of 0 to 36 months, the method comprising administering a nutritional composition comprising
  protein in an amount of 5 to 20 wt. % based on dry weight of the nutritional composition, and in an amount of 1.6 to 4.0 g per 100 kcal,
  non digestible oligosaccharides in an amount of 0.5 to 20 wt. % based on dry weight of the nutritional composition,
  at least 10 wt. % based on dry weight of the nutritional composition of a protein comprising composition fermented by lactic acid bacteria, and
  0.10 to 1.5 wt. % of the sum of lactate and lactic acid based on dry weight of the nutritional composition and wherein the sum of L-lactic acid and L-lactate is more than 50 wt. % based on the sum of total lactic acid and lactate, to the human subject with an age of 0 to 36 months.

In a preferred embodiment, the present method is for f) reducing digestive effort.

Preferably the increase or reduction of a, b, c, d and/or e and/or f) is compared to the effect of a nutritional composition not comprising a protein comprising composition fermented by lactic acid bacteria and non-digestible oligosaccharides.

The invention also concerns a method for promoting intestinal tract health in a human subject with an age of 0 to 36 months, comprising administering to the infant a nutritional composition that comprises
  protein in an amount of 5 to 20 wt. % based on dry weight of the nutritional composition, and in an amount of 1.6 to 4.0 g per 100 kcal,
  non digestible oligosaccharides in an amount of 0.5 to 20 wt. % based on dry weight of the nutritional composition,
  at least 10 wt. % based on dry weight of the nutritional composition of a protein comprising composition fermented by lactic acid bacteria, and
  0.10 to 1.5 wt. % of the sum of lactate and lactic acid based on dry weight of the nutritional composition and wherein the sum of L-lactic acid and L-lactate is more than 50 wt. % based on the sum of total lactic acid and lactate.

In other words the invention concerns the use of a protein comprising composition fermented by lactic acid bacteria and non digestible oligosaccharides in the manufacture of a nutritional composition for promoting intestinal tract health in a human subject with an age of 0 to 36 months, wherein the nutritional composition comprises
  protein in an amount of 5 to 20 wt. % based on dry weight of the nutritional composition, and in an amount of 1.6 to 4.0 g per 100 kcal,
  non digestible oligosaccharides in an amount of 0.5 to 20 wt. % based on dry weight of the nutritional composition,
  at least 10 wt. % based on dry weight of the nutritional composition of a protein comprising composition fermented by lactic acid bacteria, and
  0.10 to 1.5 wt. % of the sum of lactate and lactic acid based on dry weight of the nutritional composition and wherein the sum of L-lactic acid and L-lactate is more than 50 wt. % based on the sum of total lactic acid and lactate.

The invention can also be worded as a nutrition composition comprising
  protein in an amount of 5 to 20 wt. % based on dry weight of the nutritional composition, and in an amount of 1.6 to 4.0 g per 100 kcal,
  non digestible oligosaccharides in an amount of 0.5 to 20 wt. % based on dry weight of the nutritional composition,
  at least 10 wt. % based on dry weight of the nutritional composition of a protein comprising composition fermented by lactic acid bacteria, and
  0.10 to 1.5 wt. % of the sum of lactate and lactic acid based on dry weight of the nutritional composition and wherein the sum of L-lactic acid and L-lactate is more than 50 wt. % based on the sum of total lactic acid and lactate, for promoting intestinal tract health in a human subject with an age of 0 to 36 months.

Preferably promoting intestinal tract health is by
a increasing protein digestion efficiency,
b reducing secretion of proteases in the small and/or large intestine,
c reducing proteolytic activity in the small and/or large intestine,
d reducing the protein load entering the large intestine and/or
e reducing the fermentation of protein in the large intestine.
wherein the increase or reduction is compared to the effect of a nutritional composition not comprising a protein comprising composition fermented by lactic acid bacteria and non-digestible oligosaccharides.

The invention also concerns a method for treatment and/or prevention of diaper rashes or colics and/or cramps in a human subject with an age of 0 to 36 months, comprising administering to the infant a nutritional composition that comprises
  protein in an amount of 5 to 20 wt. % based on dry weight of the nutritional composition, and in an amount of 1.6 to 4.0 g per 100 kcal, non digestible oligosaccharides in an amount of 0.5 to 20 wt. % based on dry weight of the nutritional composition, at least 10 wt. % based on dry weight of the nutritional composition of a protein comprising composition fermented by lactic acid bacteria, and 0.10 to 1.5 wt. % of the sum of lactate and lactic acid based on dry weight of the nutritional composition and wherein the sum of L-lactic acid and L-lactate is more than 50 wt. % based on the sum of total lactic acid and lactate.

In other words the invention concerns the use of a protein comprising composition fermented by lactic acid bacteria and non digestible oligosaccharides in the manufacture of a nutritional composition for treatment and/or prevention of diaper rashes or colics and/or cramps in a human subject with an age of 0 to 36 months, wherein the nutritional composition comprises protein in an amount of 5 to 20 wt. % based on dry weight of the nutritional composition, and in an amount of 1.6 to 4.0 g per 100 kcal, non digestible oligosaccharides in an amount of 0.5 to 20 wt. % based on dry weight of the nutritional composition, at least 10 wt. % based on dry weight of the nutritional composition of a protein comprising composition fermented by lactic acid bacteria, and 0.10 to 1.5 wt. % of the sum of lactate and lactic acid based on dry weight of the nutritional composition and wherein the sum of L-lactic acid and L-lactate is more than 50 wt. % based on the sum of total lactic acid and lactate.

The invention can also be worded as a nutrition composition comprising protein in an amount of 5 to 20 wt. % based on dry weight of the nutritional composition, and in an amount of 1.6 to 4.0 g per 100 kcal, non digestible oligosaccharides in an amount of 0.5 to 20 wt. % based on dry weight of the nutritional composition, at least 10 wt. % based on dry weight of the nutritional composition of a protein comprising composition fermented by lactic acid bacteria, and 0.10 to 1.5 wt. % of the sum of lactate and lactic acid based on dry weight of the nutritional composition and wherein the sum of L-lactic acid and L-lactate is more than 50 wt. % based on the sum of total lactic acid and lactate, for use in treatment and/or prevention of diaper rashes or colics and/or cramps in a human subject with an age of 0 to 36 months.

The invention also concerns a nutritional composition comprising protein, lipids, digestible carbohydrates and non digestible oligosaccharides, wherein the protein is present in an amount of 5 to 20 wt. % based on dry weight of the nutritional composition and in an amount of 1.6 to 4.0 g per 100 kcal, wherein the lipids are present in an amount of 3 to 7 g per 100 kcal, wherein the digestible carbohydrates are present in an amount of 5 to 20 g per 100 kcal, wherein the non digestible oligosaccharides are present in an amount of 0.5 to 20 wt. % based on dry weight of the nutritional composition, further characterized in that the nutritional composition comprises at least 10 wt. % based on dry weight of the nutritional composition of a protein comprising composition fermented by lactic acid bacteria, and characterized in that the nutritional composition comprises from 0.10 to 1.5 wt. % of the sum of lactate and lactic acid based on dry weight of the nutritional composition and wherein the sum of L-lactic acid and L-lactate is more than 50 wt. % based on the sum of total lactic acid and lactate.

The invention also concerns a method for providing nutrition to a human subject with an age of 0 to 36 months, the method comprising administering the nutritional composition according to the invention to the human subject.

In other words the invention concerns the use of a nutritional composition according to the present invention for providing nutrition to a human subject with an age of 0 to 36 months.

The invention can also be worded as a nutritional composition according to the present invention for use in providing nutrition to a human subject with an age of 0 to 36 months.

Preferably according to the present invention the nutritional composition has a viscosity when administered close to that of human milk. Thus in one embodiment according to the present invention the nutritional composition does not comprise a thickener, preferably it does not comprise a thickener selected form the group consisting of locust bean gum, tara gum, gum tragacanth, guar gum, and fenugreek gum, preferably it does not comprise any of locust bean gum, tara gum, gum tragacanth, guar gum or fenugreek gum.

In one aspect the invention concerns a method for reducing proteolytic activity in the intestine of a human subject with an age of 0 to 36 months, said method comprising administering a nutritional composition to said human subject comprising protein, lipids, digestible carbohydrates and non digestible oligosaccharides, wherein the protein is present in an amount of from 5 to 20 wt. % based on dry weight of the nutritional composition, and in an amount of 1.6 to 4.0 g per 100 kcal, wherein the lipids are present in an amount of 3 to 7 g per 100 kcal, wherein the digestible carbohydrates are present in an amount of 5 to 20 g per 100 kcal, wherein the non digestible oligosaccharides are present in an amount of 0.5 to 20 wt. % based on dry weight of the nutritional composition, and wherein the non digestible oligosaccharides are selected from the group consisting of transgalactooligosaccharides, fructo-oligosaccharides and galacturonic acid oligosaccharides, more preferably the non digestible oligosaccharides comprise galacturonic acid.

For sake of clarity it is noted that the "nutritional composition" mentioned above refers to the final nutritional composition that is to be ingested or administered and the "protein comprising composition fermented by lactic acid bacteria" is comprised in the nutritional composition. The nutritional composition thus may also be referred to as "final nutritional composition" or "total nutritional composition". The "protein comprising composition fermented by lactic acid bacteria" may also be referred to as "protein comprising fermented composition" or "fermented ingredient". Also, further for sake of clarity it is noted that the "protein" part of the "protein comprising composition fermented by lactic acid bacteria" is comprised in the "5 to 20 wt. % protein" of the nutritional composition.

The term "nutritional composition" used throughout this description, i.e. the final nutritional composition that is to be ingested or administered, also refers to the "nutritional composition for human subject with an age of 0 to 36 months" specified here above. A human subject with an age of 0 to 36 months includes infants and toddlers and thus can also be referred to as an infant or toddler. Further it is noted that wherever in the present description wording like "the present nutritional composition" or "nutritional composition according to the (present) invention" is used, this also refers to the methods and uses according to the present invention.

Fermented Ingredient

Fermentation is the process of deriving energy from the oxidation of carbohydrates, such as the lactose present in milk, using an endogenous electron acceptor, which is usually an organic compound. This is in contrast to cellular respiration, where electrons are donated to an exogenous electron acceptor, such as oxygen, via an electron transport chain.

In the present invention fermentation of a milk-derived product by lactic acid producing bacteria has the common meaning of the conversion of carbohydrates present in the milk-derived product to organic acids. These organic acids formed may comprise, besides lactic acid, also other organic acids such as acetate. The carbohydrate that is fermented is preferably lactose.

Lactic acid bacteria are also referred to as lactic acid producing bacteria and include bacteria of the genus *Streptococcus, Lactococcus, Lactobacillus, Leuconostoc, Enterococcus, Oenococcus, Pediococcus*, and *Bifidobacterium*.

The present nutritional composition comprises a protein comprising composition fermented by lactic acid bacteria. The present nutritional composition preferably comprises a fermented milk-derived protein comprising composition. This fermented milk-derived protein comprising composition is obtained by incubation of a combination of milk, e.g. skim milk, or a milk derived product, e.g. whey, with at least one strain of lactic acid bacterium, such as lactococci, lactobacilli, streptococci and bifidobacteria, preferably the fermented milk-derived protein comprising composition is obtained by incubation with at least one strain selected from lactococci, lactobacilli and streptococci, preferably with at least one strain selected from streptococci. Preferably lactic acid bacteria which perform homolactic fermentation are used for fermentation, since in this case two lactic acids are produced per sugar unit and no gas is formed. Homolactic lactic acid bacteria include *Streptococcus thermophilus, Lactococcus* species, preferably *Lactococcus lactis*, and Group I lactobacilli such as *Lactobacilus acidopilus, Lactobacillus helveticus* and *Lacobacillus salivarius* and facultatively heterofermentative Lactobacilli which produce two lactic acid from hexose sugars, and which include *Lacobacillus casei, Lacobacillus paracasei, Lacobacillus rhamnosus, Lacobacillus plantarum, Lacobacillus Sakei*. Thus in one embodiment, preferably the fermented milk-derived protein comprising composition is obtained by incubation of a combination of milk, e.g. skim milk, or a milk derived product, e.g. whey, with at least one strain selected from *Streptococcus thermophilus, Lactococcus lactis, Lactobacilus acidopilus, Lactobacillus helveticus, Lacobacillus salivarius, Lacobacillus casei, Lacobacillus paracasei, Lacobacillus rhamnosus, Lacobacillus plantarum* and *Lacobacillus Sakei*, preferably the fermented milk-derived protein comprising composition is obtained by incubation with *Streptococcus thermophilus*. Preferably the combination is incubated for 10 minutes to about 6 hours. The temperature during incubation is preferably between 20 and 50° C. In one embodiment, after incubation the incubated composition is preferably subjected to a heat treatment. By this heat treatment preferably at least 90% of living microorganisms are inactivated, more preferably at least 95%. Preferably the fermented nutritional composition comprises less than $1 \cdot 10^5$ colony forming units (cfu) living lactic acid bacteria/g dry weight. The heat treatment preferably is performed at a temperature between 80 and 180° C. Inactivation of the lactic acid bacterium advantageously results in less post acidification and a safer product. This is especially advantageous when the nutritional composition is to be administered to infants or toddlers. Procedures to prepare fermented ingredients suitable for the purpose of the present invention are known per se. EP 778885, which is incorporated herein by reference, discloses in particular in example 7 a suitable process for preparing a fermented composition. FR 2723960, which is incorporated herein by reference, discloses in particular in example 6 a suitable process for preparing a fermented composition.

Briefly, a milk derived product, preferably pasteurised, containing lactose and optionally further macronutrients such as fats, preferably vegetable fats, casein, whey protein, vitamins and/or minerals etc. is concentrated, e.g. to between 15 to 50% dry matter and then inoculated with *S. thermophilus*, for example with 5% of a culture containing $10^6$ to $10^{10}$ bacteria per ml. Preferably this milk derived product comprises milk protein peptides. Temperature and duration of fermentation are as mentioned above. Suitably after fermentation the fermented protein comprising composition may be pasteurised or sterilized and for example spray dried or lyophilised to provide a form suitable to be formulated in the end product.

The bacterial strains of *S. thermophilus* that are preferably used to prepare the fermented protein comprising composition for the purpose of the present invention develop beta-galactosidase activity in the course of fermentation of the substrate. Preferably beta-galactosidase activity develops in parallel with acidity. Selection of a suitable strain of *S. thermophilus* is described in example 2 of EP 778885 and in example 1 of FR 2723960. It is preferred that in the nutritional composition according to the invention and in the use thereof there is at least part of the beta-galactosidase activity that has developed during fermentation is retained. Preferably the at least part of the beta-galactosidase activity that is retained is lactase activity. Upon digestion in the human subject, lactase activity in the nutritional composition has a beneficial effect on promoting intestinal tract health. Preferably according to the present invention, per gram dry weight the nutritional composition comprises 0.3-4 U beta-galactosidase activity, preferably the nutritional composition comprises 0.3-4 U per gram dry weight lactase activity. In a further preferred embodiment according to the present invention, the nutritional composition comprises $10^2$-$10^5$ cfu living bacteria of *S. thermophilus*, preferably the nutritional composition comprises $10^2$-$10^4$ living bacteria of *S. thermophilus*.

Preferred strains of *S. thermophilus* to prepare protein comprising fermented composition, preferably protein comprising fermented milk-derived composition for the purpose of the present invention have been deposited by Compagnie Gervais Danone at the Collection Nationale de Cultures de Microorganismes (CNCM) run by the Institut Pasteur, 25 rue du Docteur Roux, Paris, France on 23 Aug. 1995 under the accession number I-1620 and on 25 Aug. 1994 under the accession number I-1470.

Preferably, in the preparation of the protein comprising fermented composition additionally other strains of lactic acid bacteria are present or, either simultaneously or consecutively, the composition additionally is fermented by other strains of lactic acid bacteria. Other strains of lactic acid bacteria are preferably selected from the group consisting of *Lactobacillus* and Bifidobacteria, more preferably *Bifidobacterium breve*, most preferably *Bifidobacterium breve* strain deposited by Compagnie Gervais Danone at the CNCM under number I-2219 on 31 May 1999.

In one embodiment, the protein comprising composition fermented by lactic acid bacteria, comprised *Streptococcus thermophilus*, and/or *Bifidobacterium breve*. In one embodiment, the protein comprising composition fermented by lactic acid bacteria, is fermented by *Streptococcus thermophilus*, and/or *Bifidobacterium breve*.

In one embodiment, the nutritional composition comprises protein comprising composition fermented by lactic acid bacteria wherein the lactic acid bacteria are inactivated after fermentation.

Preferably the present protein comprising fermented composition is not fermented by *Lactobacillus bulgaricus*. *L. bulgaricus* fermented products are considered not suitable for infants, since in young infants the specific dehydrogenase that converts D-lactate to pyruvate is far less active than the dehydrogenase which converts L-lactate.

The protein comprising fermented composition comprises protein. The protein is preferably selected from the group consisting of non-human animal proteins, preferably milk proteins. The protein comprising fermented composition preferably contains casein, and/or whey protein, more preferably bovine whey proteins and/or bovine casein. The protein comprising fermented composition preferably comprises casein and whey proteins in a weight ratio casein: whey protein of 10:90 to 90:10, more preferably 20:80 to 80:20, even more preferably 35:65 to 55:45.

The protein comprising fermented composition comprises protein preferably providing 1.25 to 4 g per 100 kcal of the protein comprising fermented composition, preferably providing 1.5 to 3 g, even more preferable 1.7 to 2.5 g per 100 kcal. When in liquid form, the protein comprising fermented composition preferably comprises 0.5 to 6.0 g, more preferably 1.0 to 3.0 g, even more preferably 1.0 to 1.5 g protein per 100 ml, most preferably 1.0 to 1.3 g protein per 100 ml. Based on dry weight the present protein comprising fermented composition preferably comprises 5 to 20 wt. % protein, preferably at least 8 wt. %, more preferably 8 to 14 wt. %, protein even more preferably 8 to 9.5 wt. % based on dry weight of the protein comprising fermented composition.

Protein and carbohydrates are considered to have a caloric density of 4 kcal/g, fat of 9 kcal/g and non digestible oligosaccharides 2 kcal/g.

The present nutritional composition preferably comprises 10 to 100 wt. % of the protein comprising composition fermented by lactic acid bacteria, preferably a protein comprising fermented milk-derived composition, based on dry weight of the total nutritional composition. In one embodiment the present nutritional composition preferably contains 15 to 70 wt. %, preferably 15 to 50 wt. %, based on dry weight of the final nutritional composition of the protein comprising composition fermented by lactic acid bacteria. Higher concentrations of protein comprising fermented composition advantageously improve the protein digestion efficiency.

The pH of the present nutritional composition is preferably between 5.0 and 7.5, more preferably between 5.0 and 7.0, even more preferably between 5.0 and 6.0, most preferably between 5.5 and 6.0. Preferably the present nutritional composition is a liquid having a pH from 5.5 to 6.0. The present nutritional composition comprises lactic acid and/or lactate. Lactic acid and/or lactate is formed upon fermentation by lactic acid bacteria. Preferably the present nutritional composition comprises between 0.1 and 1.5 wt. % lactic acid and/or lactate, more preferably between 0.2 and 1.0 wt. %, based on dry weight of the nutritional composition. The more lactate is present the more the nutritional composition comprises of the protein comprising fermented composition. Preferably at least 50 wt. %, even more preferably at least 90 wt. %, of the sum of lactic acid and lactate is in the form of L-isomer. Thus in one embodiment the sum of L-lactic acid and L-lactate is more than 50 wt. %, more preferably more than 90 wt. %, based on the sum of total lactic acid and lactate. L-lactate and L-lactic acid is the same as L-(+)-lactate and L-(+) lactic acid.

In one embodiment the nutritional composition for infants or toddlers comprises from 0.10 to 1.5 wt. % of the sum of lactate and lactic acid based on dry weight of the nutritional composition and wherein the sum of L-lactic acid and L-lactate is more than 50 wt. % based on the sum of total lactic acid and lactate.

Protein Component

The present nutritional composition comprises a protein component. The protein used in the nutritional composition is preferably selected from the group consisting of non-human animal proteins, preferably milk proteins, vegetable proteins, such as preferably soy protein and/or rice protein, and mixtures thereof. The present nutritional composition preferably contains casein, and/or whey protein, more preferably bovine whey proteins and/or bovine casein. Thus in one embodiment the protein component comprises protein selected from the group consisting of whey protein and casein, preferably whey protein and casein, preferably the whey protein and/or casein is from cow's milk. Preferably the protein comprises less than 5 wt. % based on total protein of free amino acids, dipeptides, tripeptides or hydrolyzed protein. The present nutritional composition preferably comprises casein and whey proteins in a weight ratio casein: whey protein of 10:90 to 90:10, more preferably 20:80 to 80:20, even more preferably 35:65 to 55:45.

The wt. % protein based on dry weight of the present nutritional composition is calculated according to the Kjeldahl-method by measuring total nitrogen and using a conversion factor of 6.38 in case of casein, or a conversion factor of 6.25 for other proteins than casein. The term 'protein' or 'protein component' as used in the present invention refers to the sum of proteins, peptides and free amino acids.

The present nutritional composition comprises protein providing 1.6 to 4.0 g protein per 100 kcal of the nutritional composition, preferably providing 1.6 to 3.5 g, even more preferably 1.75 to 2.5 g per 100 kcal of the nutritional composition. In one embodiment, the present nutritional composition comprises protein providing 1.6 to 2.1 g protein per 100 kcal of the nutritional composition, preferably providing 1.6 to 2.0 g, more preferably 1.75 to 2.1 g, even more preferably 1.75 to 2.0 g per 100 kcal of the nutritional composition. In one embodiment, the nutritional composition for infants or toddlers according to the invention comprises protein preferably in an amount of less than 2.0 g per 100 kcal, preferably providing 1.6 to 1.9 g, even more preferably 1.75 to 1.85 g per 100 kcal of the nutritional composition. A too low protein content based on total calories will result is less adequate growth and development in infants and young children. When in liquid form, e.g. as a ready-to-feed liquid, the nutritional composition preferably comprises 0.5 to 6.0 g, more preferably 1.0 to 3.0 g, even more preferably 1.0 to 1.5 g protein per 100 ml, most preferably 1.0 to 1.3 g protein per 100 ml. Based on dry weight the present nutritional composition comprises 5 to 20 wt. % protein, preferably at least 8 wt. % protein based on dry weight of the total nutritional composition, more preferably 8 to 14 wt. %, even more preferably 8 to 9.5 wt. % protein based on dry weight of the total nutritional composition.

Since the use of the present nutritional composition results in an increased protein digestion efficiency and a reduced protein digestive effort, the amount of protein based on total calories, based on 100 ml or based on dry weight of the composition advantageously can be lower than that of standard infant formula. Currently the protein concentration in infant formulae is higher than in human milk, in order to ensure adequate uptake of essential amino acids. An increased protein concentration however, has disadvantages as mentioned in the section "application", it imposes a heavier burden on the kidneys of the infants and also is correlated with obesity and other adverse health effects later in life. The term 'protein' or 'protein component' as used in the present invention refers to the sum of proteins, peptides and free amino acids.

Non-Digestible Oligosaccharides

The present nutritional composition comprises non-digestible oligosaccharides. Non-digestible oligosaccharides were found to reduce the proteolytic activity in the colon. Advantageously and most preferred, the non-digestible oligosaccharides are water-soluble (according to the method disclosed in L. Prosky et al, J. Assoc. Anal. Chem 71: 1017-1023, 1988) and are preferably oligosaccharides with a degree of polymerisation (DP) of 2 to 200. The average DP of the non-digestible oligosaccharides are preferably below 200, more preferably below 100, even more preferably below 60, most preferably below 40. The non-digestible oligosaccharides are not digested in the intestine by the action of digestive enzymes present in the human upper digestive tract (small intestine and stomach). The non-digestible oligosaccharides are fermented by the human intestinal microbiota. For example, glucose, fructose, galactose, sucrose, lactose, maltose and the maltodextrins are considered digestible. The oligosaccharide raw materials may comprise monosaccharides such as glucose, fructose, fucose, galactose, rhamnose, xylose, glucuronic acid, GalNac etc., but these are not part of the oligosaccharides as in the present invention.

The non-digestible oligosaccharides included in the nutritional compositions and methods according to the present invention preferably include a mixture of non-digestible oligosaccharides. Mixtures of non-digestible oligosaccharides were found to further reduce proteolytic activity in the colon.

The non-digestible oligosaccharides are preferably selected from the group consisting of fructo-oligosaccharides, such as inulin, non-digestible dextrins, galacto-oligosaccharides, such as transgalacto-oligosaccharides, xylo-oligosaccharides, arabino-oligosaccharides, arabinogalacto-oligosaccharides, gluco-oligosaccharides, gentio-oligosaccharides, glucomanno-oligosaccharides, galactomanno-oligosaccharides, mannan-oligosaccharides, isomalto-oligosaccharides, nigero-oligosaccharides, glucomanno-oligosaccharides, chito-oligosaccharides, soy oligosaccharides, uronic acid oligosaccharides, sialyloligosaccharides, such as 3-sialyllactose (3-SL), 6-SL, lactosialylterasaccharide (LST) a,b,c, disialyllactoNtetraose (DSLNT), sialyl-lactoNhexaose (S-LNH), DS-LNH, and fuco-oligosaccharides, such as (un)sulphated fucoidan oligosaccharides, 2'-fucosyllactose (2'-FL), 3-FL, difucosyllactose, lacto-N-fucopenatose, (LNFP) I, II, III, V, Lacto-N-neofucopenaose (LNnFP), Lacto-N-difucosyl-hexaose (LNDH), and mixtures thereof, even more preferably selected from the group consisting of fructo-oligosaccharide, such as inulin, galacto-oligosaccharide, such as transgalacto-oligosaccharide, uronic acid oligosaccharide and fuco-oligosaccharide and mixtures thereof, even more preferably transgalacto-oligosaccharide, inulin and/or uronic acid oligosaccharides, most preferably transgalacto-oligosaccharides. In one embodiment in the composition or methods according to the present invention, the non digestible oligosaccharides are selected from the group consisting of transgalacto-oligosaccharides, fructo-oligosaccharides and galacturonic acid oligosaccharides and mixtures of thereof. The non-digestible oligosaccharides are preferably selected from the group consisting of β-galacto-oligosaccharide, α-galacto-oligosaccharide, and galactan. According to a more preferred embodiment non-digestible oligosaccharides are β-galacto-oligosaccharide. Preferably the non-digestible oligosaccharides comprises galacto-oligosaccharides with β(1,4), β(1,3) and/or β(1,6) glycosidic bonds and a terminal glucose. Transgalacto-oligosaccharide is for example available under the trade name Vivinal®GOS (Borculo Domo Ingredients, Zwolle, Netherlands), Bi2muno (Clasado), Cup-oligo (Nissin Sugar) and Oligomate55 (Yakult).

The non-digestible oligosaccharides preferably comprise fructo-oligosaccharides. A fructo-oligosaccharide may in other context have names like fructopolysaccharides, oligofructose, polyfructose, polyfructan, inulin, levan and fructan and may refer to oligosaccharides comprising β-linked fructose units, which are preferably linked by β(2,1) and/or β(2,6) glycosidic linkages, and a preferable DP between 2 and 200. Preferably, the fructo-oligosaccharide contains a terminal β(2,1) glycosidic linked glucose. Preferably, the fructo-oligosaccharide contains at least 7β-linked fructose units. In a further preferred embodiment inulin is used. Inulin is a type of fructo-oligosaccharide wherein at least 75% of the glycosidic linkages are β(2,1) linkages. Typically, inulin has an average chain length between 8 and 60 monosaccharide units. A suitable fructo-oligosaccharide for use in the compositions of the present invention is commercially available under the trade name Raftiline®HP (Orafti). Other suitable sources are raftilose (Orafti), fibrulose and fibruline (Cosucra) and Frutafit and frutalose (Sensus).

Preferably the mixture of galactooligosaccharides and fructooligosaccharides is present in a weight ratio of from 1/99 to 99/1, more preferably from 1/19 to 19/1, even more preferably from 1 to 19/1. This weight ratio is particularly advantageous when non-digestible oligosaccharide A has a low DP and non-digestible oligosaccharide B has a relatively high DP.

Preferably the mixture of short chain fructooligosaccharides and long chain fructooligosaccharides is present in a weight ratio of from 1/99 to 99/1, more preferably from 1/19 to 19/1, even more preferably from 1 to 19/1.

In a more preferred embodiment the present nutritional composition further comprises uronic acid oligosaccharides. The term uronic acid oligosaccharide as used in the present invention refers to an oligosaccharide wherein at least 50 number % of the monosaccharide units present in the oligosaccharide is one selected from the group consisting of guluronic acid, mannuronic acid, galacturonic acid, iduronic acid, riburonic acid and glucuronic acid. In a preferred embodiment the uronic acid oligosaccharide comprises at least 50 number % galacturonic acid based on total uronic acid units in the uronic acid oligosaccharide. The uronic acid oligosaccharides used in the invention are preferably prepared from degradation of pectin, pectate, alginate, chondroitine, hyaluronic acids, heparine, heparane, bacterial carbohydrates, and/or sialoglycans, more preferably of pectin and/or alginate, even more preferably of pectin, most preferably polygalacturonic acid. Preferably the degraded pectin is prepared by hydrolysis and/or beta-elimination of fruit and/or vegetable pectins, more preferably apple, citrus and/or sugar beet pectin, even more preferably apple, citrus and/or sugar beet pectin degraded by at least one lyase. Preferably, the non-digestible oligosaccharide is galacturonic acid oligosaccharide.

In a preferred embodiment, at least one of the terminal uronic acid units of the uronic acid oligosaccharide has a double bond. The double bond effectively protects against attachment of pathogenic bacteria to intestinal epithelial cells. This is advantageous for infants and toddlers. Preferably, one of the terminal uronic acid units comprises the C4-C5 double bond. The double bond at terminal uronic acid unit can for example be obtained by enzymatic hydrolysis of pectin with lyase. The uronic acid oligosaccharide can be derivatised. The uronic acid oligosaccharide may be methoxylated and/or amidated.

Preferably, the present nutritional composition comprises the non-digestible oligosaccharides transgalacto-oligosaccharide, fructo-oligosaccharide and a pectin degradation product.

The weight ratio transgalacto-oligosaccharide:fructo-oligosaccharide:pectin degradation product is preferably (20 to 2):1:(1 to 3), more preferably (12 to 7):1:(1 to 2).

Preferably, the present invention relates to a nutritional composition, wherein the non-digestible oligosaccharide is selected from the group consisting of fructo-oligosaccharide, galacto-oligosaccharide and uronic acid oligosaccharide, wherein the uronic acid oligosaccharide is preferably galacturonic acid oligosaccharide.

Preferred is a mixture of transgalacto-oligosaccharide with an average DP below 10, preferably below 6 and a fructo-oligosaccharide with an average DP below 10, preferably below 6. Most preferred is a mixture of fructo-oligosaccharide with an average DP below 10, preferably below 6 and a fructo-oligosaccharide with an average DP above 7, preferably above 11, even more preferably above 20. Such a mixture synergistically reduces colonic protein fermentation and proteolytic activity. Most preferred is a mixture of transgalacto-oligosaccharide with an average DP below 10, preferably below 6 and a fructo-oligosaccharide with an average DP above 7, preferably above 11, even more preferably above 20. Such a mixture synergistically reduces colonic protein fermentation and proteolytic activity.

The present nutritional composition preferably comprises 0.5 to 20 wt. % total non-digestible oligosaccharide, more preferably 1 to 10 wt. %, even more preferably 2 to 10 wt. %, most preferably 2.0 to 7.5 wt. %, based on dry weight of the present composition. Based on 100 ml the present enteral composition preferably comprises 0.1 to 2.5 wt. % total non-digestible oligosaccharide, more preferably 0.2 to 1.5 wt. %, even more preferably 0.4 to 1.5 wt. %, based on 100 ml of the present composition.

Nutritional Composition

The present nutritional composition is preferably particularly suitable for providing the complete daily nutritional requirements to a human subject with an age below 36 months, more preferably a human infant. The present nutritional composition is not a yogurt, since yoghurt contains by convention *L. bulgaricus* (Codex Standard for fermented Milks Codex Stan 243-2003).

The present nutritional composition comprises a digestible carbohydrate component. Preferred digestible carbohydrate components are lactose, glucose, sucrose, fructose, galactose, maltose, starch and maltodextrin. Lactose is the main digestible carbohydrate present in human milk. The present nutritional composition preferably comprises lactose. As the present nutritional composition comprises a protein comprising composition fermented by lactic acid bacteria, the amount of lactose is reduced compared to its source due to the fermentation whereby lactose is converted into lactate and/or lactic acid. Therefore in the preparation of the present nutritional composition lactose is preferably added. Preferably the present nutritional composition does not comprise high amounts of carbohydrates other than lactose. Compared to digestible carbohydrates such as maltodextrin, sucrose, glucose, maltose and other digestible carbohydrates with a high glycemic index, lactose has a lower glycemic index and is therefore preferred. The present nutritional composition preferably comprises digestible carbohydrate, wherein at least 35 wt. %, more preferably at least 50 wt. %, more preferably at least 60 wt. %, more preferably at least 75 wt. %, even more preferably at least 90 wt %, most preferably at least 95 wt % of the digestible carbohydrate is lactose. Based on dry weight the present nutritional composition preferably comprises at least 25 wt. % lactose, preferably at least 40 wt. %, more preferably at least 50 wt % lactose. Advantageously, the present nutritional composition is relatively low in protein and relatively high in lactose. Thus in one embodiment, preferably the present nutritional composition comprises 1.6 to 2.1 g protein per 100 kcal of the nutritional composition, preferably 1.6 to 2.0 g protein per 100 kcal of the nutritional composition and the digestible carbohydrate component comprises at least 60 wt. % lactose based on total digestible carbohydrate, more preferably at least 75 wt. %, even more preferably at least 90 wt. % lactose based on total digestible carbohydrate.

When in liquid form, e.g. as a ready-to-feed liquid, the nutritional composition preferably comprises 3.0 to 30 g digestible carbohydrate per 100 ml, more preferably 6.0 to 20, even more preferably 7.0 to 10.0 g per 100 ml. Based on dry weight the present nutritional composition preferably comprises 20 to 80 wt. %, more preferably 40 to 65 wt. % digestible carbohydrates. Based on total calories the nutritional composition comprises 5 to 20 g digestible carbohydrates per 100 kcal, more preferably 8 to 15 g.

The present nutritional composition comprises a lipid component. The lipid component of the present nutritional composition provides 3 to 7 g per 100 kcal of the nutritional composition, preferably the lipid component provides 4 to 6 g per 100 kcal. When in liquid form, e.g. as a ready-to-feed liquid, the nutritional composition preferably comprises 2.1 to 6.5 g lipid per 100 ml, more preferably 3.0 to 4.0 g per 100 ml. Based on dry weight the present nutritional composition preferably comprises 12.5 to 40 wt. % lipid, more preferably 19 to 30 wt. %.

Preferably the lipid component comprises the essential fatty acids alpha-linolenic acid (ALA), linoleic acid (LA) and/or long chain polyunsaturated fatty acids (LC-PUFA). The LC-PUFA, LA and/or ALA may be provided as free fatty acids, in triglyceride form, in diglyceride form, in monoglyceride form, in phospholipid form, or as a mixture of one of more of the above. Preferably the present nutritional composition contains at least one, preferably at least two lipid sources selected from the group consisting of rape seed oil (such as colza oil, low erucic acid rape seed oil and canola oil), high oleic sunflower oil, high oleic safflower oil, olive oil, marine oils, microbial oils, coconut oil, palm kernel oil and milk fat.

The present nutritional composition is not human breast milk. The present nutritional composition comprises a lipid component and a protein component and a digestible carbohydrate component. The nutritional composition according to the invention or the nutritional composition used according to the invention preferably comprises other fractions, such as vitamins, minerals, trace elements and other micronutrients in order to make it a complete nutritional composition. Preferably the nutritional composition is selected from the group consisting of an infant formula, toddler milk or formula and growing up milk, more preferably form the group consisting of an infant formula. An infant formula is defined as a formula for use in infants and can for example be a starter formula, intended for infants of 0 to 4 to 6 months of age or a follow on formula, intended for infants of 4 to 6 months until 12 months of age. A toddler or growing up milk or formula is intended for children of 12 to 36 months of age. In one embodiment the nutritional composition is an infant formula. Infant formulae comprise vitamins, minerals, trace elements and other micronutrients according to international directives. The lipid component provides 3 to 7 g lipid per 100 kcal, preferably 4 to 6 g per 100 kcal, the protein component provides 1.6 to 4 g per 100 kcal, preferably 1.75 to 2.5 g per 100 kcal and the digestible carbohydrate component provides 5 to 20 g per 100 kcal, preferably 8 to 15 g per 100 kcal of the final nutritional composition. Preferably the present nutritional composition comprises a lipid component providing 4 to 6 g per 100 kcal, a protein component providing 1.6 to 1.9 g per 100 kcal, more preferably 1.75 to 1.85 g per 100 kcal and a digestible carbohydrate component providing 8 to 15 g per 100 kcal of the final nutritional composition. In one embodiment, the lipid component provides 3 to 7 g lipid per 100 kcal, preferably 4 to 6 g per 100 kcal, the protein component provides 1.6 to 2.1 g per 100 kcal, preferably 1.6 to 2.0 g per 100 kcal and the digestible carbohydrate component provides 5 to 20 g per 100 kcal, preferably 8 to 15 g per 100 kcal of the final nutritional composition and wherein preferably the digestible carbohydrate component comprises at least 60 wt. % lactose based on total digestible carbohydrate, more preferably at least 75 wt. %, even more preferably at least 90 wt. % lactose based on total digestible carbohydrate.

The amount of total calories is determined by the sum of calories derived from protein, lipids, digestible carbohydrates and non digestible oligosaccharides.

In one embodiment the nutritional composition is in a liquid form. In another embodiment the nutritional composition is a powder suitable for making a liquid nutritional composition after reconstitution with an aqueous solution, preferably with water. Preferably the infant or toddler formula is a powder to be reconstituted with water. Preferably the liquid composition has a viscosity below 100 mPa·s, more preferably below 60 mPa·s, more preferably below 35 mPa·s, even more preferably below 6 mPa·s as measured in a Brookfield viscometer at 20° C. at a shear rate of 100 $s^{-1}$. A low viscosity is important for infant or follow on formula, since it mimics the viscosity of breast milk and can then be administered via a teat.

In order to meet the caloric requirements of an infant or toddler, the nutritional composition preferably comprises 45 to 200 kcal/100 ml liquid. For infants the nutritional composition has more preferably 60 to 90 kcal/100 ml liquid, even more preferably 65 to 75 kcal/100 ml liquid. This caloric density ensures an optimal ratio between water and calorie consumption. For toddlers, human subjects with an age between 12 and 36 months, the nutritional composition more preferably has a caloric density between 45 and 65, even more preferably between 50 and 60 kcal/100 ml. The osmolarity of the present composition is preferably between 150 and 420 mOsmol/l, more preferably 260 to 320 mOsmol/l. The low osmolarity aims to further reduce the gastrointestinal stress.

When the nutritional composition is in a liquid form, the preferred volume administered on a daily basis is in the range of about 80 to 2500 ml, more preferably about 200 to 1200 ml per day. Preferably, the number of feedings per day is between 1 and 10, preferably between 3 and 8. In one embodiment the nutritional composition is administered daily for a period of at least 2 days, preferably for a period of at least 4 weeks, preferably for a period of at least 8 weeks, more preferably for a period of at least 12 weeks, in a liquid form wherein the total volume administered daily is between 200 ml and 1200 ml and wherein the number of feedings per day is between 1 and 10.

Application

In the context of the present invention, 'prevention' of a disease or certain disorder also means 'reduction of the risk' of a disease or certain disorder and also means 'treatment of a person at risk' of said disease or said certain disorder.

The inventors have found that upon consumption of the nutritional composition of the present invention the amount of endogenous proteolytic enzymes that was detected at the terminal ileum was significantly reduced compared to the amount detected upon consumption of a standard, not a fermented ingredient containing nutritional composition. In addition, even though the daily protein intake was higher, the apparent and true protein digestibility was the highest in the group consuming the nutritional composition of the present invention.

The nutritional composition of the present invention was found to reduce digestive effort. Digestive effort is defined as the amount of protease activity secreted per gram of proteins ingested.

The nutritional composition of the present invention was found to improve protein digestion efficiency. Protein digestion efficiency is defined as the amount of protein ingested per arbitrary unit (AU) of protease activity. The nutritional composition of the present invention was found to reduce the loss of endogenous protein, such as the loss of endogenously formed proteases. This was in particular the case for trypsin and/or chymotrypsin and/or elastase. Trypsin and chymotrypsin are in an infant the most important digestive proteases, since gastric pepsin is less active due to a higher pH in the stomach. In addition, proteases have been found to stimulate the endogenous loss of other proteins, such as mucins.

The nutritional composition of the present invention was found to reduce the protein load entering the colon.

Thus upon feeding the nutritional composition of the present invention, the release of endogenous protease, digestive effort, endogenous protein loss in the small intestine and the protein load entering the colon is advantageously reduced as well as the proteolytic activity of the microbiota in the colon. The nutritional composition of the present invention will have an improved effect on reducing protein fermentation and proteolytic activity in the colon and will have a beneficial effect regarding proteolytic activity reduction along the entire, i.e. both small and large, intestinal tract.

Therefore the nutritional composition of the present invention is advantageously used as nutrition for infants or toddlers, for use in preventing and/or treatment of diaper rashes or in promoting intestinal tract health by reducing digestive effort, improving or increasing protein digestion efficiency, reducing endogenous protein loss, reducing endogenous secretion of proteases, reducing colonic protein fermentation and/or reducing the protein load entering the colon.

The finding that protein digestion efficiency is increased, and endogenous protein loss is decreased also advantageously enables the formulation of an infant or toddler formula with lower protein concentrations than used so far.

The effects described herein are observed compared to the situation before administration of the nutritional composition and/or to the situation compared to the administering of a standard nutritional composition not comprising the protein comprising fermented composition and non digestible oligosaccharides. It was found that these effects observed also come closer to the effects occurring in human milk fed infants compared to standard infant formula fed infants, since it was found that the proteolytic activity in faecal samples of exclusively breast fed human infants was lower than that of infants fed with a standard formula.

By these effects mentioned above the nutritional composition of the present invention improves intestinal tract health. In one embodiment the present nutritional composition for infants is for use in promoting intestinal tract health. Preferably the intestinal tract health is selected from the group consisting of i) increased intestinal barrier function and ii) the use in prevention and/or treatment of a disorder selected from the group consisting of constipation, abdominal pain, abdominal discomfort, colics, cramps, abdominal bloating, abdominal distention, irritable bowel syndrome and intestinal inflammation. In one embodiment the intestinal tract health is selected from the group consisting of inflammatory bowel disease (IBD) such as ulcerative colitis and diarrhoegenic irritable bowel syndrome (IBS-D).

Preferably the intestinal tract health is selected from the group consisting of constipation, abdominal pain, abdominal discomfort, colics, cramps, abdominal bloating, abdominal distention and irritable bowel syndrome. In one embodiment the intestinal tract health is selected from intestinal inflammation. In one embodiment the nutritional composition of the present invention improves intestinal tract health by prevention and/or treatment of constipation. Constipation may be assessed or described as a decreased frequency of defecation and/or an increase stool consistency In particular the reduced amount of protein entering the colon will result in a more saccharolytic and less proteolytic activity of the intestinal microbiota. Fermentation of sugars instead of amino acids will result in a lower pH of the colon and/or in a reduced formation of toxic metabolites such as indols, phenols and amines. This also will result in more Bifidobacteria and/or Lactobacilli and/or less pathogenic bacteria in the intestinal microbiota. The amounts of bacteria can be expressed as cfu per g faeces and/or as a percentage based on cfu of total bacteria. Such improved intestinal microbiota will result in reduced intestinal infections and/or reduction in diarrhea. In particular the reduced amount of proteases, more specifically serine proteases such as trypsin and chymotrypsin, will result in a reduced cleavage of PAR-2 with effect of an increased intestinal barrier function. An increased barrier function will result in reduced translocation of toxins, allergens and pathogens and hence in an advantageous effect on infection, diarrhea and/or inflammation. Also reduced PAR-2 cleavage will result in less abdominal pain perception Increased faecal proteolytic activity is in particular associated with inflammatory bowel disease (IBD) such as ulcerative colitis and with diarrhoegenic irritable bowel syndrome (IBS-D). Thus in one embodiment the nutritional composition of the present invention is used for treatment and/or prevention of inflammatory bowel disease such as ulcerative colitis and diarrhoegenic irritable bowel syndrome (IBS-D). Increased faecal proteolytic activity is in particular associated with the occurrence of diaper rashes. Therefore the present nutritional composition of the invention is preferably for use in treatment and/or prevention of diaper rashes. Furthermore, lower synthesis of proteases, concomitant with increase protein digestibility results in less energy and protein loss, which improves growth and development.

Colonic fermentation of proteins will result in changes of quality or quantity of gas formation and hence an increased abdominal bloating and/or abdominal distention and/or flatulence Hence the present nutritional composition will have an effect in reduction of abdominal bloating and/or abdominal distention and of disorders resulting thereof. Activation of protease activated receptors increases pain perception and has a negative effect on gut barrier function. Lower proteolytic activity may thus contribute to the increased prevention and/or treatment of colics or cramps. Cramps can be assessed when an infant performs arching of the back, and colics can be assessed when there is excessive crying time. In one embodiment the nutritional composition of the present invention is used for treatment and/or prevention of colics and/or cramps.

All these above observed and mentioned effects are particularly important in young human subjects, since they need to grow and develop, have a more immature intestinal barrier and a less developed intestinal microbiota. In other words, in young human subjects, improving protein digestive effort, regulation of the endogenous protein release, restriction of protein loss, and decrease of protein load in the colon is most important. Intestinal tract development is a complex process. It is feasible that intestinal tract leakiness renders infants during the first months of life more susceptible to elevated levels of proteolytic activity, which may trigger low levels of inflammation and increased pain perception. This may explain the beneficial effects of the present nutritional composition which induces less endogenous protease release. Hence, the nutritional composition is preferably used for feeding a human infant.

In one embodiment the invention concerns a method, preferably a non-therapeutic method, for
a increasing protein digestion efficiency,
b reducing secretion of proteases in the small and/or large intestine,
c reducing proteolytic activity in the small and/or large intestine,
d reducing the protein load entering the large intestine and/or
e reducing the fermentation of protein in the large intestine
in a human subject with an age of 0 to 36 months, the method comprising administering a nutritional composition according to the invention to the human subject with an age of 0 to 36 months, wherein the increase or reduction is compared to the effect of a nutritional composition not comprising a protein comprising composition fermented by lactic acid bacteria and non-digestible oligosaccharides. Preferably for this method the nutritional composition comprises lactose.

In one embodiment the protease is a serine protease and the proteolytic activity is the proteolytic activity of a serine protease, more preferably a serine protease selected from the group consisting of trypsin, chymotrypsin and elastase.

The present nutritional composition is used for providing nutrition to a human subject with an age of 0 to 36 months. In one embodiment the present nutritional composition is used for providing nutrition to an infant of 0 to 18 months, even more preferably an infant with an age of 12 months of age or below. In one embodiment the present nutritional composition is used for providing nutrition to a toddler of 18 to 36 months, most preferably a toddler with an age of 18 to 30, or 24 months. The present nutritional compositionis preferably is enteraly administered, more preferably orally.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one. Wt. means weight.

EXAMPLES

Example 1

A double-blind, placebo-controlled, randomised, prospective study with parallel group design was conducted in healthy term born infants until the infants' age of one year.

The test groups were:

Group 1: Infants on full breastfeeding for at least 4 months (N=43).

Group 2: Infants on full formula feeding after 2 months at the latest, receiving a standard non-hydrolysed cow's milk based formula (N=41).

Group 3: Infants on full formula feeding after 2 months at the latest, receiving a standard non-hydrolysed cow's milk based formula containing an mixture of non-digestible carbohydrates (0.8 g/100 ml) of neutral and acidic oligosaccharides in a weight ratio of 85:15. As neutral oligosaccharides transgalactooligosaccharides (source VivinalGOS), and long chain oligosaccharides (source raftiniln HP) in a 9:1 weight ratio were use. As acidic oligosaacrides uronic acid oligosaccharides derived from pectin degradation were used. (N=36).

Stool samples were collected at week 16 after birth and stored at −20° C. until further analysis. Faecal proteolytic activity in the faecal supernatant was measured with the EnzCheck protease fluorescence based assay kit (E6638, Invitrogen, Carlsbad, Ca, USA) for detecting metallo-, serine and sulfhydryl proteases. Faecal samples were 10× diluted in 1×PBS, homogenized for 5 min and centrifuged at 13.000 rpm for 3 minutes to remove large particles. 100 µl (100× diluted) supernatant was added to 100 µl working BODIPY casein (10 µg BODIPY casein). Increase in fluorescence was measured at 25° C. for a period of 10 minutes. Porcine pancreatin (Sigma, P1750) was used to prepare a calibration curve. To determine the origin of protease activity, the specific serine protease inhibitor AEBSF (Sigma, A8456) was added in each analysis with a final concentration of 5 mM. Total protein in the faecal supernatants was determined using the BCA method (Pierce). Faecal proteolytic activity was expressed as arbitrary units (AU) based on pancreatin activity in USP (standard unit for activity according to United States Pharmacopeia) per milligram faecal protein content. Statistics was performed with the Mann-Whitney U test.

Results:

Results are shown in Table 1. The faecal proteolytic activity in the group on standard infant formula was significantly higher compared to the breast-fed group and the group on standard infant formula containing the oligosaccharide mixture. Faecal proteolytic activity was similar between the groups on breast milk and standard infant formula containing the non digestible oligosaccharide mixture.

TABLE 1

Mean proteolytic activity (AU/mg protein) in the faecaes of infants fed on breast meil (group 1), a control infant formula (group 2) or a formula with non digestible carbohydrates (Group 3)

| Diet | Proteolytic activity (SE) | P value* vs group 1 | P value* vs group 2 |
|---|---|---|---|
| Group 1 | 313 (21) | | 0.032 |
| Group 2 | 406 (33) | 0.032 | |
| Group 3 | 309 (26) | 0.488 | 0.020 |

*Mann-Whitney U test.

The proteolytic activity was mainly derived from serine proteases (i.e. pancreatic enzymes or produced by colonic microbiota), since the specific serine protease inhibitor AEBSF blocked proteolytic activity with more than 70%.

These experiments are indicative for reducing colonic proteolytic activity and reduced protein fermentation in the presence of non digestible oligosaccharides.

Example 2

Piglet Experiments with Fermented Infant Formula

To investigate protein digestion in vivo, pigs are first choice since they highly resemble human digestive physiology (Miller et al. 1987, Annu Rev Nutr, 7:361-82) and generate comparable true ileal nitrogen and amino acid (AA) digestibilities (Deglaire et al. 2009, Br J Nutr, 102(12):1752-9, Rowan et al. 1994, Br J Nutr, 71(1):29-42). In addition, a study by Moughan et al. has shown that three-week-old piglets can be used as a model for 6-month-old infants (Moughan et al. 1991, J Nutr, 121(10):1570-4). Therefore, AA digestibility of a fermented and standard infant formula (IF) was tested in a piglet model. A hydrolyzed formula (Nutrilon Pepti) was used to correct for endogenous AA losses according to the peptide alimentation method (Rutherfurd et al. 1998, J Dairy Sci, 81(4):909-17).

Six age- and weight matched male piglets (average weight 4.9 kg) were housed in groups from 2 weeks of age. At three weeks of age they received a T-cannula at the distal part of the terminal ileum after overnight fasting and were housed individually thereafter. From day 31 onwards the pigs received the following diets:

Diet 1: Lactofidus-1, a commercially available Infant Milk Formula marketed under brand name Gallia, comprising 100% of a fermented milk-derived composition. Lactofidus is produced by fermenting with *S. thermophilus* and comprising *B. breve*. A heat treatment is employed to inactivate the lactic acid bacteria. It contains 1.1 wt. % lactic acid+lactate based on dry weight, which is at least for 95% L-lactic acid/lactate. It comprises 12.2 g protein per 100 g dry weight of which 60 wt. % casein and 40 wt. % whey protein. The pH is 5.6.

Diet 2: Nutrilon-2, a standard non-fermented follow on formula marketed under the brand name Nutricia, comprising non-hydrolysed protein, 9.3 g per 100 g dry weight of which 50 wt. % non-hydrolysed whey protein and 50 wt. % casein. The pH is 6.8.

Diet 3: Pepti-2, an IMF marketed under the brand name of Nutricia comprising 11.2 g protein per 100 g dry weight in the form of 100 wt. % extensively hydrolysed whey protein. The pH is 6.4.

The fermented, standard and hydrolyzed powdered IMF was diluted in demineralised water (37° C.) to a final dry matter content of 21.0%, 22.05% and 21.45%, respectively (the protein content being 2.46, 2.05, and 2.55 g/100 ml).

Chromium oxide was added to the IMF powder as indigestible marker. Until day 31, the piglets received a 1:1:1 w/w/w mixture of diet 1, 2 and 3.

From day 31 to day 36 the piglets received either diet 1, 2 or 3 in a Latin Square design according to the feeding scheme of Table 1. Pigs were fed at 7:00 h, 9:30 h, 14:00 h and 16:00 h. Ileal digesta were collected at day 32, 34 and 36 from 8.00 h till 17.00 h, via the T cannula in small bags which were stored on ice immediately when filled. All digesta samples were weighed, pH measured and stored at −20° C. until further processing. For enzymatic activity measurements a subsample (2 ml) was centrifuged (13.000 g for 10 minutes at 4° C.) and supernatants were aliquoted and stored at −80° C.

TABLE 2

Feeding scheme

| Piglet | Day 31-32 | Day 33-34 | Day 35-36 |
|---|---|---|---|
| 1 | 1 | 2 | 3 |
| 2 | 1 | 3 | 2 |
| 3 | 2 | 1 | 3 |
| 4 | 2 | 3 | 1 |
| 5 | 3 | 1 | 2 |
| 6 | 3 | 2 | 1 |

Dry matter (DM) (gravimetry at 80° C.), chromium oxide (Cr) (inductively coupled plasma mass spectrometry), crude protein (CP) (Kjeldahl method, N×6.25) and amino acid (AA) composition (HPLC after 6M HCL hydrolysis) were analyzed in freeze-dried digesta samples and diet powders.

Total proteolytic activity in the ileal digesta was determined using the EnzCheck protease fluorescence based assay kit (E6638, Invitrogen, Carlsbad, Ca, USA) for detecting metallo-, serine and sulfhydryl proteases. Digesta were diluted 750× with 10 mM Tris-HCl, pH 7.8, and 100 µl samples were added to 100 µl working BODIPY casein (10 µg BODIPY casein). Increase in fluorescence was measured at 25° C. for a period of 10 minutes. Porcine pancreatin (Sigma, P1750) was used to prepare a calibration curve. To determine the origin of protease activity, the specific serine protease inhibitor AEBSF (Sigma, A8456) was added in each analysis with a final concentration of 5 mM. Activity is expressed as arbitrary unit (AU) (based on pancreatin activity in USP).

Trypsin activity was measured by using $N_\alpha$-Benzoyl-L-Arginne Ethyl Ester (BAEE, Sigma B4500) as substrate and measuring the absorbance change at 25° C. 253 nm (according to the manufacturer's instructions). Bovine trypsin (Sigma, T9201) was used to prepare a calibration curve. Activity is expressed as arbitrary unit (AU) (based on trypsin activity in U).

Chymotrypsin was measured by using $N_\alpha$-Benzoyl-L-Tyrosine Ethyl Ester (BTEE, Sigma B6125) as substrate and measuring the absorbance change at 25° C. at 256 nm. Bovine chymotrypsin (Sigma, C3142) was used to prepare a calibration curve. Activity is expressed as arbitrary unit (AU) (based on chymotrypsin activity in U).

Elastase activity was measured by using SucAla3-PNA (S4760, Sigma) as substrate and porcine elastase (E7885, Sigma) was used to prepare a calibration curve. Activity is expressed as arbitrary unit (AU) (based on elastase activity in U).

Equations used to calculate AA digestibility (units are in µg/g DMI):

$$\text{Ileal AA flow} = \text{ileal AA} \times \frac{Cr \text{ diet}}{Cr \text{ digesta}}$$

$$\text{Endogenous AA flow} = \text{ileal AA}(\text{MW} > 10 \text{ } kD) \times \frac{Cr \text{ diet}}{Cr \text{ digesta}}$$

$$\text{Apparent ileal AA digestibility}(\%) = \frac{\text{AA intake} - \text{ileal AA flow}}{\text{AA intake}} \times 100\%$$

True ileal AA digestibility(%) =

$$\frac{\text{AA intake} - (\text{ileal AA flow} - \text{endogenous AA flow})}{\text{AA intake}} \times 100\%$$

The results were analyzed using Univariate Analysis of Variance (GLM procedure). Differences between diets were considered significant with p<0.05 according to the LSD test.

The results in Table 3 show that the pH of the ileal digesta was the same. Also osmolarity was the same. The amount of crude protein intake was highest in the hydrolysed formula and in the fermented formula. Interestingly, the amount of total protein in the ileal digesta and the relative amount of protein based on protein intake was significantly lower in the piglets consuming fermented formula than in the other two groups. This flow of protein to the colon is therefore lowest in piglets consuming fermented formula. The apparent and true ileal crude protein digestibility was higher in piglets consuming the fermented formula than in the group consuming the standard formula. The apparent and true ileal amino acid digestibility was higher in piglets consuming the fermented formula than in the group consuming the standard formula. The same is applicable for the majority of the individual amino acids. The true glycine digestibility differs most notably. This is indicative for a decrease in endogenous protein secretion. Endogenous amino acid flow was mainly rich in glutamic acid, threonine, aspartic acid, proline and serine.

TABLE 3

Diet intake, ileal digesta characteristics & ileal AA digestibility

|  | Nutrilon | Lactofidus | Pepti | Pooled SE |
|---|---|---|---|---|
| DM intake (g/day) | 403$^a$ | 388$^b$ | 391$^b$ | 3.641 |
| CP intake (g/day) | 37.4$^a$ | 45.4$^b$ | 46.4$^c$ | 0.317 |
| Total AA intake (g/day) | 39.1$^a$ | 47.7$^b$ | 50.2$^c$ | 0.347 |
| Ileal digesta osmolarity (mOsm/kg) | 305 | 305 | 309 | 3.3 |
| Ileal digesta pH | 7.91 | 7.95 | 7.90 | 0.06 |
| Ileal digesta CP (g/g CPI) | 0.16$^a$ | 0.08$^b$ | 0.16$^a$ | 0.01 |
| Total ileal digesta CP (g/day) | 5.96$^a$ | 3.64$^b$ | 7.27$^c$ | 0.279 |
| Apparent ileal crude protein digestibility (%) | 84.2$^a$ | 92.0$^b$ | x | 0.81 |
| Apparent ileal AA digestibility (%) | 89.1$^a$ | 94.4$^b$ | x | 0.53 |
| Alanine | 85.0$^a$ | 91.1$^b$ | x | 0.81 |
| Arginine | 85.8$^a$ | 93.1$^b$ | x | 0.68 |
| Aspartic acid | 88.6$^a$ | 93.8$^b$ | x | 0.51 |
| Cystine | 85.1 | 89.5 | x | 1.06 |

TABLE 3-continued

Diet intake, ileal digesta characteristics & ileal AA digestibility

|  | Nutrilon | Lactofidus | Pepti | Pooled SE |
|---|---|---|---|---|
| Glutamic acid | 93.1$^a$ | 96.3$^b$ | x | 0.29 |
| Glycine | 48.5 | 78.5$^b$ | x | 4.81 |
| Histidine | 88.9$^a$ | 94.5$^b$ | x | 0.51 |
| Iso-leucine | 91.9$^a$ | 95.8$^b$ | x | 0.34 |
| Leucine | 93.4$^a$ | 96.5$^b$ | x | 0.29 |
| Lysine | 91.1$^a$ | 96.1$^b$ | x | 0.31 |
| Methionine | 93.9$^a$ | 97.2$^b$ | x | 0.36 |
| Phenylalanine | 88.8$^a$ | 94.6$^b$ | x | 0.40 |
| Proline | 90.1$^a$ | 95.4$^b$ | x | 0.59 |
| Serine | 84.6$^a$ | 92.2$^b$ | x | 0.63 |
| Threonine | 79.0$^a$ | 88.1$^b$ | x | 1.05 |
| Tyrosine | 90.7$^a$ | 94.7$^b$ | x | 0.37 |
| Valine | 90.6$^a$ | 95.2$^b$ | x | 0.54 |
| True ileal crude protein digestibility (%) | 94.2$^a$ | 99.9$^b$ | x | 0.89 |
| True ileal AA digestibility (%) | 97.1$^a$ | 100.8$^b$ | x | 0.61 |
| Alanine | 96.7$^a$ | 101.2$^b$ | x | 0.87 |
| Arginine | 94.4$^a$ | 99.4$^b$ | x | 0.82 |
| Aspartic acid | 97.3$^a$ | 101.3$^b$ | x | 0.58 |
| Cystine | 97.0$^a$ | 102.2$^b$ | x | 1.01 |
| Glutamic acid | 98.6$^a$ | 100.6$^b$ | x | 0.34 |
| Glycine | 72.4$^a$ | 97.4$^b$ | x | 4.74 |
| Histidine | 96.4$^a$ | 100.3$^b$ | x | 0.63 |
| Iso-leucine | 99.1$^a$ | 101.7$^b$ | x | 0.42 |
| Leucine | 98.5$^a$ | 100.7$^b$ | x | 0.35 |
| Lysine | 96.6$^a$ | 100.6$^b$ | x | 0.37 |
| Methionine | 98.8$^a$ | 100.9$^b$ | x | 0.42 |
| Phenylalanine | 96.3$^a$ | 100.1$^b$ | x | 0.53 |
| Proline | 97.4$^a$ | 100.8$^b$ | x | 0.66 |
| Serine | 96.6$^a$ | 101.3$^b$ | x | 0.73 |
| Threonine | 96.5$^a$ | 102.7$^b$ | x | 1.12 |
| Tyrosine | 97.8 | 100.0 | x | 0.53 |
| Valine | 98.5$^a$ | 101.3$^b$ | x | 0.43 | x = not determined.
$^{a-c}$Values with different letters within the same row are different (p < 0.05)

TABLE 4

Ileal proteolytic enzyme activities

|  | Nutrilon | Lactofidus | Pepti | Pooled SE |
|---|---|---|---|---|
| Total proteolytic activity |  |  |  |  |
| AU × 10$^3$/8 h | 1599$^a$ | 477$^b$ | 759$^b$ | 140 |
| AU × 10$^3$/g CPI | 41.4$^a$ | 10.5$^b$ | 16.5$^b$ | 3.3 |
| Trypsin activity |  |  |  |  |
| AU × 10$^3$/8 h | 908$^a$ | 334$^b$ | 621$^c$ | 74 |
| AU/g CPI | 23.9$^a$ | 7.4$^b$ | 13.5$^c$ | 1.6 |
| Chymotrypsin activity |  |  |  |  |
| AU/8 h | 665$^a$ | 294$^b$ | 486$^{ab}$ | 73 |
| AU/g CPI | 17.2$^a$ | 6.5$^b$ | 10.3$^b$ | 1.8 |
| Elastase activity |  |  |  |  |
| AU/8 h | 191$^a$ | 69$^b$ | 123$^c$ | 13 |
| AU/CPI | 4.78$^a$ | 1.45$^b$ | 2.47$^c$ | 0.27 |

NS = not significant, x = not determined.
$^{a-c}$Values with different letters within the same row are different (p < 0.05)

The results in Table 4 show that the amount of proteolytic activity secreted during the 8 h of collection is lowest in piglets consuming Lactofidus, the fermented infant formula, when compared with standard non fermented formula or a hydrolysed, predigested IMF. This is the case for total proteolytic activity as well as for trypsin and chymotrypsin. This is the case for elastase activity. This effect is also observed when based on amount of protein intake.

The proteolytic activity is mainly derived from serine proteases (i.e. pancreatic enzymes such as trypsin and chymotrypsin), since the specific serine protease inhibitor AEBSF blocked proteolytic activity with more than 90%. So, the amount of proteolytic activity entering the colon is lower upon consumption of a fermented formula, which makes it more similar to the situation in breast fed infants (see example 1).

Surprisingly the apparent and true protein digestibility is the highest when consuming the fermented formula, even though the lowest amount of proteases is formed. This means that the digestive efficiency (in [Protein ingested/protease activity in AU) is higher. Likewise, the amount of proteolytic activity per g protein intake is lower, which is indicative of a decreased digestive effort.

Example 3

Low Protein Infant Formula

A powdered infant formula, which after reconstitution with water to a ready to feed liquid infant formula comprising per 100 ml:
about 13.0 g dry matter, 66 kcal
1.2 g protein (bovine whey protein/casein in 1/1 weight ratio), 9.8 wt % based on dry weight, 1.8 g per 100 kcal.
7.3 g digestible carbohydrate (7.3 g sugars of which of which 7.1 g lactose) (11.4 g/100 kcal),
3.36 g fat (mainly vegetable fat). (50.9 g/100 kcal)
0.8 g non-digestible oligosaccharides of scGOS (source Vivinal GOS) and 1cFOS (source RaftilinHP) in a 9:1 wt ratio, of which 0.6 g classifies as dietary fiber and 0.2 g being indigestible saccharides present in the scGOS, which is classified as carbohydrates.

Of this composition 30% based on dry weight is derived from lactofidus-1 as described in example 2. The composition comprises about 0.33 wt. % lactic acid+lactate based on dry weight, of which at least 95% is L-lactate/lactic acid. The composition further comprises vitamins, minerals, trace elements and other micronutrients according to international directives for infant formula.

The pH after reconstitution is 6.2.

Example 4

Infant Formula

A powdered infant formula, which after reconstitution with water to a ready to feed liquid infant formula comprising per 100 ml:
about 13.7 g dry matter, 66 kcal
1.35 g protein (bovine whey protein/casein in 1/1 weight ratio), 11 wt. % based on dry weight, 2.0 g/100 kcal
8.2 g digestible carbohydrate (of which 5.6 g lactose, and 2.1 g maltodextrin)
3.0 g fat (mainly vegetable fat).
0.8 g non-digestible oligosaccharides of scGOS (source Vivinal GOS) and 1cFOS (source RaftilinHP) in a 9:1 wt ratio.

Of this composition 50% based on dry weight is derived from lactofidus-1 as described in example 2. The composition comprises about 0.55 wt. % lactic acid+lactate based on dry weight, of which at least 95% is L-lactic acid/lactate. The composition further comprises vitamins, minerals, trace elements and other micronutrients according to international directive 2006/141/EC for infant formula.

The infant formula is intended for promoting intestinal tract health and/or increasing intestinal barrier function and/or prevention and/or treatment of constipation, abdominal pain, abdominal discomfort, colics, cramps, abdominal bloating, abdominal distention irritable bowel syndrome, ulcerative colitis, diarrhoegenic irritable bowel syndrome or intestinal inflammation, and/or prevention and/or treatment of diaper rashes.

Example 5

Formula for Toddlers

A liquid ready to drink intended children of 12 to 36 months of age, comprising per 100 ml:
About 56 kcal
1.5 g protein (bovine whey protein/casein in 1/1 weight ratio), 2.7 g/100 kcal
6.6 g digestible carbohydrate (of which over 95 wt % lactose)
1.94 g fat (mainly vegetable fat).
1.2 g non-digestible oligosaccharides of scGOS (source Vivinal GOS) and 1cFOS (source RaftilinHP) in a 9:1 wt ratio.
Of this composition 15% based on dry weight is derived from lactofidus-1 as described in example 2. The composition comprises about 0.17 wt. % lactic acid+lactate based on dry weight, of which at least 95% is L-lactic acid/lactate. The composition further comprises vitamins, minerals, trace elements and other micronutrients as known in the art.
The pH of this composition is 6.6

The invention claimed is:
1. A nutritional composition comprising:
(a) protein, wherein the protein is present in an amount of from 5 to 20 wt. % based on dry weight of the nutritional composition, and in an amount of 1.6 to 2.0 g per 100 kcal
(b) lipids, wherein the lipids are present in an amount of 3 to 7 g per 100 kcal
(c) digestible carbohydrates, and wherein the digestible carbohydrates are present in an amount of 5 to 20 g per 100 kcal
(d) non digestible oligosaccharides, wherein the non digestible oligosaccharides are present in an amount of 0.5 to 20 wt. % based on dry weight of the nutritional composition,
(e) at least 10 wt. %, based on dry weight of the nutritional composition, of a protein comprising composition fermented by lactic acid bacteria, and
(f) from 0.10 to 1.5 wt. % of the sum of lactate and lactic acid, based on dry weight of the nutritional composition, wherein the sum of L-lactic acid and L-lactate is more than 50 wt. % based on the sum of total lactic acid and lactate.

2. The composition according to claim 1, wherein the protease is a serine protease and the proteolytic activity is the proteolytic activity of a serine protease.
3. The composition according to claim 2, wherein the serine protease is selected from the group consisting of trypsin, chymotrypsin and elastase.
4. The composition according to claim 1, wherein the lactic acid bacteria is selected from the group consisting of *Streptococcus thermophilus, Lactococcus lactis, Lactobacillus acidopilus, Lactobacillus helveticus, Lacobacillus salivarius, Lacobacillus casei, Lacobacillus paracasei, Lacobacillus rhamnosus, Lacobacillus plantarum* and *Lacobacillus Sakei*.
5. The composition according to claim 1, wherein the lactic acid bacteria is *Streptococcus thermophilus*.
6. The composition according to claim 5, wherein the nutritional composition comprises $10^2$-$10^5$ cfu living *Streptococcus thermophilus* per gram dry weight of the nutritional composition.
7. The composition according to claim 1, wherein the composition is a liquid having pH from 5.5 to 7.0.
8. The composition according to claim 1, wherein the nutritional composition comprises digestible carbohydrate and wherein at least 75 wt. % of the digestible carbohydrate is lactose.
9. The composition according to claim 1, wherein the non digestible oligosaccharides are selected from the group consisting of galacto-oligosaccharides, fructo-oligosaccharides, uronic acid oligosaccharides, gluco-oligosaccharides, xylo-oligosaccharides, mannan-oligosaccharides, arabino-oligosaccharides, glucomanno-oligosaccharides, galacto-manno-oligosaccharides, soy oligosaccharides, isomalto-oligosaccharides, non digestible dextrin, arabinogalacto-oligosaccharides, gentio-oligosaccharides, nigero-oligosaccharides, glucomanno-oligosaccharides, chito-oligosaccharides, sialyl-oligosaccharides, and fuco-oligosaccharides.
10. The composition according to claim 1, comprising at least two non digestible oligosaccharides selected from the group consisting of galacto-oligosaccharides, fructo-oligosaccharides, uronic acid oligosaccharides, gluco-oligosaccharides, xylo-oligosaccharides, mannan-oligosaccharides, arabino-oligosaccharides, glucomanno-oligosaccharides, galactomanno-oligosaccharides, soy oligosaccharides, isomalto-oligosaccharides, non digestible dextrin, arabinogalacto-oligosaccharides, gentio-oligosaccharides, nigero-oligosaccharides, glucomanno-oligosaccharides, chito-oligosaccharides, sialyl-oligosaccharides, and fuco-oligosaccharides.
11. The composition according to claim 1, wherein the non digestible oligosaccharides are selected from the group consisting of transgalacto-oligosaccharides, fructo-oligosaccharides and galacturonic acid oligosaccharides, and mixtures of thereof.

* * * * *